(12) United States Patent
Yamauchi et al.

(10) Patent No.: US 12,006,463 B2
(45) Date of Patent: *Jun. 11, 2024

(54) POLYMERIZABLE LIQUID CRYSTAL HAVING A QUINOXALINE-HYDRAZONE CORE

(71) Applicant: ROLIC TECHNOLOGIES AG, Allschwil (CH)

(72) Inventors: Shinnosuke Yamauchi, Amagasaki (JP); Fabien Nekelson, Chiba (JP); Sabrina Chappellet, Village-Neuf (FR)

(73) Assignee: ROLIC TECHNOLOGIES AG, Allschwil (CH)

( * ) Notice: Subject to any disclaimer, the term of this patent is extended or adjusted under 35 U.S.C. 154(b) by 144 days.

This patent is subject to a terminal disclaimer.

(21) Appl. No.: 17/611,644

(22) PCT Filed: Jun. 26, 2020

(86) PCT No.: PCT/EP2020/068081
§ 371 (c)(1),
(2) Date: Nov. 16, 2021

(87) PCT Pub. No.: WO2020/260621
PCT Pub. Date: Dec. 30, 2020

(65) Prior Publication Data
US 2022/0251450 A1 Aug. 11, 2022

(30) Foreign Application Priority Data

Jun. 28, 2019 (EP) ..................... 19183356
Aug. 28, 2019 (EP) ..................... 19194041

(51) Int. Cl.
G02F 1/1333 (2006.01)
C07D 241/44 (2006.01)
C08F 122/22 (2006.01)
C09K 19/34 (2006.01)
C09K 19/38 (2006.01)
C09K 19/04 (2006.01)

(52) U.S. Cl.
CPC ........ C09K 19/3861 (2013.01); C07D 241/44 (2013.01); C08F 122/22 (2013.01); C09K 19/345 (2013.01); C09K 19/3804 (2013.01); C09K 2019/0444 (2013.01); C09K 2019/0448 (2013.01)

(58) Field of Classification Search
CPC ............ C09K 19/3804; C09K 19/3861; C09K 19/24; C09K 19/3452; C09K 19/345; C09K 2019/0444; C09K 2019/0448; G02F 1/1333; G02F 1/137; C07D 241/44; C08F 122/22
See application file for complete search history.

(56) References Cited

U.S. PATENT DOCUMENTS

| | | | |
|---|---|---|---|
| 4,122,027 A | 10/1978 | Cole, Jr. | |
| 4,401,369 A | 8/1983 | Jones | |
| 4,565,424 A | 1/1986 | Huffman et al. | |
| 4,667,020 A | 5/1987 | Etzbach et al. | |
| 5,389,285 A | 2/1995 | Shannon et al. | |
| 5,539,074 A | 7/1996 | Herr et al. | |
| 6,107,427 A | 8/2000 | Herr et al. | |
| 6,201,087 B1 | 3/2001 | Herr et al. | |
| 6,632,909 B2 | 10/2003 | Buchecker et al. | |
| 7,959,990 B2 | 6/2011 | Cherkaoui et al. | |
| 2017/0174992 A1 | 6/2017 | Ootsuki | |
| 2022/0251450 A1* | 8/2022 | Yamauchi | C09K 19/24 |
| 2022/0298418 A1* | 9/2022 | Chappellet | C09K 19/067 |

FOREIGN PATENT DOCUMENTS

| | | |
|---|---|---|
| EP | 2 703 385 A1 | 3/2014 |
| EP | 2 857 424 A1 | 4/2015 |
| JP | 2016-128403 A | 7/2016 |
| JP | 2017-125009 A | 7/2017 |
| WO | 2012/141245 A1 | 10/2012 |
| WO | 2012/147904 A1 | 11/2012 |
| WO | 2016/104317 A1 | 6/2016 |
| WO | 2017/043437 A1 | 3/2017 |

OTHER PUBLICATIONS

International Search Report of PCT/EP2020/068081 dated Oct. 19, 2020 [PCT/ISA/210].
Written Opinion of PCT/EP2020/068081 dated Oct. 19, 2020 [PCT/ISA/237].

* cited by examiner

Primary Examiner — Geraldina Visconti
(74) Attorney, Agent, or Firm — Sughrue Mion, PLLC

(57) ABSTRACT

The invention relates to novel anisotropic compounds of formula (I)

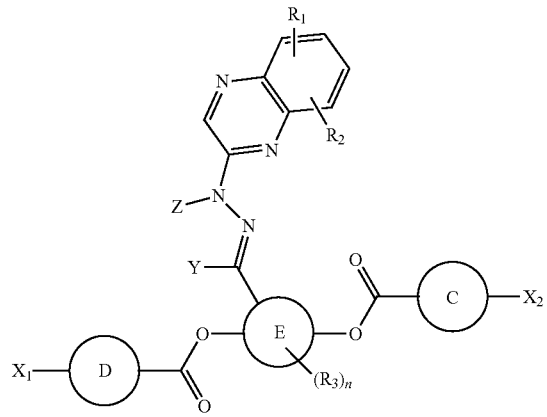

as well as liquid crystalline mixtures, films and electro-optical devices comprising the compound.

16 Claims, 1 Drawing Sheet

POLYMERIZABLE LIQUID CRYSTAL HAVING A QUINOXALINE-HYDRAZONE CORE

CROSS REFERENCE TO RELATED APPLICATIONS

This application is a National Stage of International Application No. PCT/EP2020/068081, filed Jun. 26, 2020, claiming priority to European Patent Application No. 19183356.5, filed Jun. 28, 2019, and European Patent Application No. 19194041.0, filed Aug. 28, 2019.

BACKGROUND OF THE INVENTION

The present invention relates to novel polymerizable anisotropic Liquid Crystals (LCPs) compounds having a quinoxaline-hydrazone core, to compositions comprising such LCPs compounds and to optical films comprising such LCPs compounds or compositions. Optical films comprising the LCPs according to the present invention shown reverse retardation pattern of polarized light over a wide wavelength band. Finally, the present invention relates to optically anisotropic articles comprising such LCPs compounds or comprising optical films comprising such LCPs compounds such as, e.g. flat displays, TVs, smartphones, tablets.

Optical films prepared from curable LCPs compounds (LCP films) are well known to a skilled person and are used in the preparation of optical devices. Examples of optical films are retardation films or polarizers. Retardation films are a type of optical elements which change the polarization state of light passing through the same. When light passes through a retardation film, the polarization direction of the light changes because of the birefringence and the thickness of the film. Quarter-wave retardation plates convert linearly polarized light into circularly polarized light, and half-wave retardation plates convert the plane of vibration of linearly polarized light by 90°. Such retardation films can achieve conversion of specific monochromatic light so that λ/4 or λ/2 retardation occurs. However, the known retardation films have the drawback that the polarized light that passes through is converted into coloured polarized light. Further, a polarization state distribution corresponding to each wavelength occurs for polarized white light. Therefore, it is impossible to achieve accurate λ/4 or λ/2 retardation over the entire wavelength band. To improve such drawbacks, there is the need to develop retarder films having a wavelength dispersion which is higher in the long wavelength than in the short wavelength. Another issue in preparation of retardation films, also known as retarders, is to prepare high performing films at a small charge of materials.

There is, therefore, a need for new LCP compounds that may be used in the preparation of an optical film as described above, which significantly reduces the aforementioned disadvantages. The present invention addresses that need.

Several anisotropic LCP compounds are already known in the art, but there is still the demand to develop new LCP compounds with improved uniform conversion of polarized light over a wider wavelength. Few examples of such anisotropic LCP compounds are disclosed in WO2012/147904, WO2016/104317, WO2017/043437 and JP2016/128403.

LCP films are generally manufactured by method well-known by the skilled person. This involves coating an organic solution of a cross-linkable LCP or LCP mixture onto a substrate provided with an orientation layer or onto a substrate which has previously been treated by the rubbing technique. Or other aligning techniques for liquid crystals may be used. The organic solvent is subsequently removed to give a well-oriented, solvent-free LCP layer, which in turn is cross-linked to fix the liquid crystalline properties ordered structure. The desired optical performance of such films depends crucially on some physical parameters which the anisotropic LCP material has to fulfil simultaneously. Such properties are a low melting point or a low tendency to crystallise when cooled below melting point (supercooling), good solubility in organic solvents, good miscibility with other LCPs, good aligning properties on orientation layers, and the ability to form an adjustable tilt out of the substrate plane essentially free of tilt domains and disclinations. Tilt domains are regions within the LCP film in which the long axes of the LCP molecules form tilt angles out of the plane of the substrate of the same size but in opposite direction. Disclinations are borderlines of neighbouring tilt domains where LCP molecules of opposite tilt angles are adjacent. These tilt domains and disclinations result in both a disturbance in the uniform appearance of the film and an inhomogeneous optical performance.

SUMMARY OF THE INVENTION

It is a first object of the present invention to provide an anisotropic LCP compound as described by formula (I) and to compositions comprising at least one of said compounds and at least one additive and/or a solvent.

It is a further object of the present invention to provide an optical film comprising at least one of said anisotropic LCP compound and to methods of its preparation, to the use of said optical film as retardation film achieving uniform conversion of polarized light and to devices comprising said optical films and their manufacturing.

DETAILED DESCRIPTION OF THE INVENTION

Figure 1:
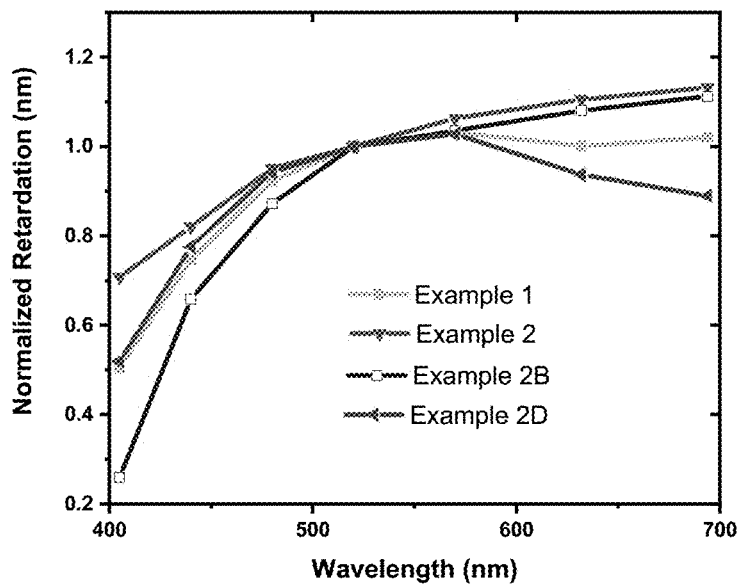
FIG. 1. shows the wavelength dispersion of the Birefringence for examples 1, 2, 2B and 2D.

The first aspect of the invention provides a compound of formula (I)

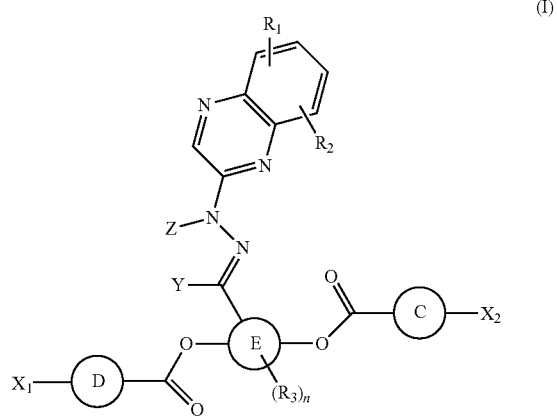

In the compounds of formula (I), $R_1$, $R_2$ and $R_3$ are independently from each other selected from the group consisting of hydrogen, $C_1$-$C_{12}$ straight or branched alkyl chain, $C_3$-$C_{12}$ alkenyl, $C_1$-$C_{12}$ alkoxy, $C_3$-$C_{12}$ alkenyloxy, —$(CH_2)_m$—$C(CH_3)_3$, $NO_2$, CN, COR, —COOR, —OCOR, —CONR'R, —NR'COR, OCOOR, —OCONR'R, —NR'COOR, —F, —Cl, —CF$_3$ and —OCF$_3$;

in which m is an integer between 0 and 12;

R is selected from the group consisting of hydrogen, an $C_{1-18}$ alkyl group, an $C_{3-18}$ alkenyl group with the double bond at 3-position or higher, —$(CH_2)_p$—C—$(CF_3)_3$, CN and unsubstituted or substituted phenyl ring, wherein the substituent of the phenyl ring is selected from the group consisting of $C_1$-$C_6$ straight or branched alkyl chain, $C_1$-$C_6$ alkoxy, —C—$(CH_3)_3$, halogen, —CF$_3$, $NO_2$, CN, COR''', —COOR''', —OCOR''', —CONR''R''', —NR''COR''', OCOOR''', —OCONR''R''', —NR''COOR''', —F, —Cl, —CF$_3$ and —OCF$_3$;

in which

R'' is selected from the group consisting of hydrogen, a lower alkyl group and a lower alkenyl group;

R''' is selected from the group consisting of hydrogen, an $C_{1-18}$ alkyl group and an $C_{3-18}$ alkenyl group with the double bond at 3-position or higher;

p is an integer between 0 and 12;

R' is selected from the group consisting of hydrogen, lower alkyl, lower alkenyl and lower alkoxy;

and in which n is 0, 1, 2 or 3.

Preferably, $R_1$, $R_2$ and $R_3$ are independently from each other selected from the group consisting of hydrogen, lower alkyl, lower alkenyl, lower alkoxy, lower alkenyloxy —F, and —CF$_3$.

Most preferably, $R_1$, $R_2$ and $R_3$ are independently from each other selected from the group consisting of hydrogen, methyl, methoxy, —F, —C—$(CH_3)_3$ and —CF$_3$.

Y is selected from the group consisting of H, or substituted or unsubstituted alkyl group having 1 to 12 carbon atoms.

Z is selected from the group consisting of hydrogen, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, wherein one or more carbon atoms may be replaced by —O—, —COO—, —OCO—, —OOC—, —O(CO)O—, —N—, —NR$^a$—, —CON—, —CO—R$^b$, —NH—R$^a$, wherein R$^a$ is a $C_1$-$C_{12}$ alkyl group, R$^b$ and R$^c$ are independently from each other a substituted or unsubstituted alkyl group having 1 to 20 carbon atoms, or an organic group having 2 to 30 carbon atoms that includes at least one aromatic ring, or a substituted or unsubstituted alkenyl group having 2 to 20 carbon atoms, or a substituted or unsubstituted cycloalkyl group having 3 to 12 carbon atoms.

Preferably, Z is selected from the group consisting of hydrogen and substituted or unsubstituted alky group having 1 to 12 carbon atoms.

Rings C and D are independently from each other selected from the group consisting of phenyl, biphenyl, naphthyl, cycloalkyl, preferably cyclohexyl, bicycloalkyl, preferably bicyclohexyl,

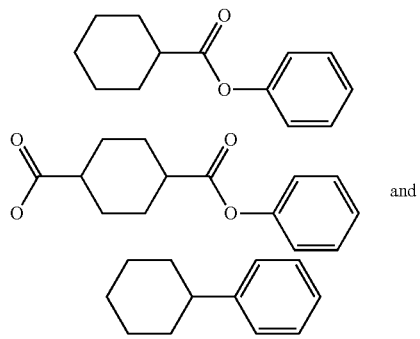

with the proviso that at least one of rings C or D contains an aromatic ring.

Preferably, rings C and D are independently from each other phenyl or cyclohexyl, most preferably both rings C and D are phenyl rings.

Ring E is selected from the group consisting of phenyl, biphenyl and naphthyl.

Preferably ring E is a phenyl ring.

Substituents $X_1$ and $X_2$ are independently from each other selected from the group consisting of hydrogen, $C_1$-$C_{12}$ substituted or unsubstituted straight or branched alkyl chain, $C_3$-$C_{12}$ substituted or unsubstituted straight chain or branched alkenyl chain and $C_1$-$C_{12}$ alkoxy, wherein one or more carbon atoms may be replaced by —O—, —COO—, —OCO—, —OOC—, —O(CO)O—, —N—, —NR$^a$—, —CON—, wherein R$^a$ is a $C_1$-$C_{12}$ alkyl group; or substituents $X_1$ and $X_2$ independently from each other are represented by the group of formula (II)

(formula II)

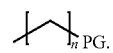

In the group of formula (II), n is an integer between 0 and 24, wherein one or more carbon atoms may be replaced by —O—, —COO—, —OCO—, —OOC—, —O(CO)O—, —N—, —NR$^a$—, —CON—, wherein R$^a$ is a $C_1$-$C_{12}$ alkyl group.

Substituent PG in the group of formula (II) represents a polymerisable group selected from the group consisting of $CH_2$=C(Ph)-, $CH_2$=CW—COO—, $CH_2$=CH—COO-Ph-, $CH_2$=CW—CO—NH—, $CH_2$=CH—O—, $CH_2$=CH—OOC—, Ph-CH=CH—, $CH_2$=CH-Ph-, $CH_2$=CH-Ph-O—, R$^b$-Ph-CH=CH—COO—, R$^b$—OOC—CH=CH-Ph-O— and 2-W-epoxyethyl; in which W represents H, Cl, Ph or a lower alkyl and R$^b$ represents a lower alkyl with the proviso that when R$^b$ is attached to a phenylene group (-Ph-) it may also represent hydrogen or a lower alkoxy. Preferably, PG represents an acrylate or a methacrylate group.

Preferably, substituents $X_1$ and $X_2$ are selected from the group consisting of hydrogen, $C_1$-$C_{12}$ substituted or unsubstituted straight or branched alkyl chain, $C_3$-$C_{12}$ substituted or unsubstituted straight chain or branched alkenyl chain and $C_1$-$C_{12}$ alkoxy when rings C and D are independently from each other cyclohexyl or contain a cyclohexyl.

Preferably, if rings C or D are independently from each other aromatic rings or they contain an aromatic ring, more preferably if C or D are independently from each other phenyl rings or contain phenyl rings, the group of formula (II), is selected from

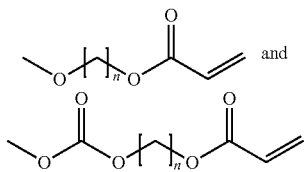

wherein n has the same meaning as given above or their corresponding methacrylates.

By the term "lower alkyl" it should be understood to include a $C_{1-6}$ achiral, branched or straight-chained alkyl group. Examples of lower alkyl groups that may be present in the compounds of the invention include methyl, ethyl, propyl, butyl, pentyl hexyl and the like.

By the term "lower alkenyl" it should be understood to include $C_{3-6}$ achiral, branched or straight-chained alkenyl group in which the double bond is at position 2- or higher. Examples of lower alkenyl groups that may be present in the compounds of the invention include 2-propenyl, 3-butenyl, 3-isopentenyl, 4-pentenyl, 5-hexenyl, 4-isohexenyl and the like.

By the term "lower alkoxy" it should be understood to include $C_{1-6}$ achiral, branched or straight-chained alkoxy group. Examples of lower alkoxy groups that may be present in the compounds of the invention include methoxy, ethoxy, propoxy, butoxy, pentoxy hexoxy and the like.

By the term "lower alkenyloxy" it should be understood to include $C_{3-6}$ achiral, branched or straight-chained alkenyloxy group in which the double bond is at position 2- or higher. Examples of lower alkenyloxy groups that may be present in the compounds of the invention include 2-propenyloxy, 3-butenyloxy, 4-pentenyloxy, 5-hexenyloxy and the like.

The polymerizable anisotropic LCP compounds of the invention may be readily prepared using procedures well known to a skilled person and few non-limiting procedures are provided in the examples.

The starting materials are commercially available or may be readily prepared and are well known to a skilled person.

A polymerizable anisotropic LCP compound material as used within the context of this application shall mean a liquid crystal material, which comprises liquid crystal monomers and/or liquid crystal oligomers and/or liquid crystal polymers and/or cross-linked liquid crystals. In case the liquid crystal material comprises liquid crystal monomers, such monomers may be polymerized, typically after anisotropy has been created in the LCP material, for example due to contact with an aligning layer or by rubbing. Polymerization may be initiated by thermal treatment and/or by exposure to actinic light, which preferably comprises UV-light. An anisotropic LCP-material may comprise only a single type of liquid crystal compound, but may also comprise additional polymerizable and/or non-polymerizable compounds, wherein not all of the compounds have to be liquid crystal compounds. In case of optical films, LCP monomers are applied on top of a photo-aligning layer or on top of a rubbed surface. After the alignment information of the photo-aligning layer or of the rubbed surface has been transferred to the LCP monomers, the monomers are polymerized and/or cross-linked in order to solidify the LCP material. It is understood that a polymerized or crosslinked polymers according to the present invention may contain only anisotropic LCP compounds of formula (I) alone, and in this case the polymer is a homopolymer, or the polymerized or crosslinked polymers may contain further different monomers, and in this case the polymer is a copolymer. The further different monomer may or may not have LCP properties.

The anisotropic LCP compounds according to the present invention overcome the drawbacks described previously of the LCP compounds of the prior art. Further, the anisotropic LCP compounds according to the present invention have excellent solubility and low temperature processability.

A further object of the present invention relates to a composition comprising the anisotropic LCP compound as described by formula (I) and at least an additive. The additives can be selected from the following: antioxidants, initiators, such as photoinitiators, accelerators, dyes, inhibitors, activators, fillers, chain transfer inhibitor, pigments, anti-static agents, flame-retardant agents, thickeners, thixotropic agents, surface-active agents, viscosity modifiers, extending oils, plasticizers, tackifiers, catalysts, sensitizers, stabilizers, lubricating agents, dispersing agents, a polymeric binder and/or monomeric compounds which can be converted into the polymeric binder by polymerization, or, in the case of emulsion coatings and printing inks, a dispersion auxiliary, hydrophobing agents, adhesive agents, flow improvers, defoaming agents, deaerators, diluents, auxiliaries, colorants, dyes and pigments, curing inhibitors, a chiral additive, isotropic or anisotropic fluorescent and/or non-fluorescent dyes, in particular dichroic dyes. The solvent that may be used in the preparation of such liquid crystalline compositions include but not limited to acetone, cyclopentanone (CP), cyclohexanone (CH), methyl isobutyl ketone (MIBK), methylethylketone (MEK), N,N-dimethylformamide (DMF), N-methylpyrrolidone (NMP), N-ethylpyrrolidone, N-vinylpyrrolidone, N,N-dimethylacetamide, (AN), tetrahydrofuran (THF), 1,3-dioxolane (DXG), ethylene glycol, dipropylene glycol, butylcarbitol, ethylcarbitol acetate, dipropylene glycol monomethyl ether, ethyl acetate (EA), 1-methoxy-2-propanol acetate (MPA), gamma-butyrolactone (BL), propylene glycol monoacetate, propylene glycol diacetate, dipropylene glycol monomethyl ether, dimethyl sulfoxide (DMSO). Most preferred solvents are cyclopentanone (CP), cyclohexanone (CH), methyl isobutyl ketone (MIBK), methylethylketone (MEK), ethyl acetate (EA), 1-methoxy-2-propanol acetate (MPA), 1,3-dioxolane (DXG), dimethyl sulfoxide (DMSO).

A further preferred object of the present invention relates to a composition comprising the anisotropic LCP compound of formula (I), LCP mixture, and at least one solvent, selected from cyclohexanone, toluene and cyclopentanone, and/or an additive.

A further preferred embodiment of the present invention is a composition, a LCP mixture, comprising the anisotropic compound of formula (I), which preferably has a shelf life stability over more than 3 months with no crystallization.

The present invention relates to an optical film comprising at least one of the anisotropic LCP compounds or compositions according to the present invention. An example of an optical film is an antireflective film that is produced by combining the optical film according to the present invention with a polarizer.

The anisotropic LCP compounds or the composition comprising the anisotropic LCP compounds can be applied on a support. The support may be rigid or flexible and can have any form or shape. In principle it may consist of any material. Preferably, the support comprises plastic, glass or metal or is a silicon wafer. In case the support is flexible, it is preferred that the support is a plastic or metal foil. Preferably, the surface of the support is flat. For some applications the support may comprise topographical surface structures, such as microstructures like micro lenses or micro-prisms, or structures exhibiting abrupt changes of the shape, such as rectangular structures. Preferably, the support is transparent. The support may also have been subjected to a treatment before coating with the anisotropic LCP compound according to the present invention.

The support may be moving during the deposition of the anisotropic LCP compounds or the composition comprising the anisotropic LCP compounds. For example, a layer of the LCP mixture may be produced in a continuous roll to roll process by depositing the material composition onto a moving flexible foil, which is preferably plastic or metallic. The resulting film may then be wound on a roll together with the support foil or the film may be released from the support and is then wound as a free standing film, without the support.

The support may have additional layers, such as photoaligning layer, organic, dielectric or metallic layers. The layers can have different functions, for example an organic layer can be coated as a primer layer which increases compatibility of the materials to be coated with the support. Metallic layers may be used as electrodes, for example when used in electrooptical devices such as displays, or could have the function as a reflector. The support may also be an optical element or device which has certain functions, such as a substrate for an LCD, which might, for example, comprise thin film transistors, electrodes or color filters. In another example, the support is a device comprising an OLED layer structure. The support could also be a a polarizer, such as a polarizing film or a sheet polarizer, a reflective polarizer, such as the commercially available Vikuity™ DBEF film.

In the context of the present invention, a "photoaligning layer" is made of a material in which anisotropic properties, a photo-orientable substance, can be induced upon exposure to aligning light. In addition the term "photoaligning layer" refers to a layer that has been aligned by exposure to aligning light. For the present invention the induced anisotropy must be as such that it provides alignment capability for the adjacent layer comprising e.g. the anisotropic LCP compounds of formula (I). The term "alignment direction" shall refer to the preferred direction that is induced in the adjacent layer, for example the alignment direction is the direction in which the LCP compounds would be aligned.

Photo-orientable substances incorporate photo-orientable moieties, which are capable of developing a preferred direction upon exposure to aligning light and thus creating anisotropic properties. Such photo-orientable moieties preferably have anisotropic absorption properties. Typically, such moieties exhibit absorption within the wavelength range from 230 to 500 nm. Preferably, the photo-orientable moieties exhibit absorption of light in the wavelength range from 300 to 450 nm, more preferred are moieties, which exhibit absorption in the wavelength range from 310 to 380 nm.

Preferably the photo-orientable moieties have carbon-carbon, carbon-nitrogen, or nitrogen-nitrogen double bonds.

For example, photo-orientable moieties are substituted or un-substituted azo dyes, anthraquinone, coumarin, mericyanine, 2-phenylazothiazole, 2-phenylazobenzthiazole, stilbene, cyanostilbene, fluorostilbene, cinnamonitrile, chalcone, cinnamate, cyanocinnamate, stilbazolium, 1,4-bis(2-phenylethylenyl)benzene, 4,4'-bis(arylazo)stilbenes, perylene, 4,8-diamino-1,5-naphthoquinone dyes, aryloxy-carboxylic derivatives, arylester, N-arylamide, polyimide, diaryl ketones, having a ketone moiety or ketone derivative in conjugation with two aromatic rings, such as for example substituted benzophenones, benzophenone imines, phenylhydrazones, and semicarbazones.

Preparation of the anisotropically absorbing materials listed above are well known as shown, e.g. by Hoffman et al., U.S. Pat. No. 4,565,424, Jones et al., in U.S. Pat. No. 4,401,369, Cole, Jr. et al., in U.S. Pat. No. 4,122,027, Etzbach et al., in U.S. Pat. No. 4,667,020, and Shannon et al., in U.S. Pat. No. 5,389,285.

Preferably, the photo-orientable moieties comprise arylazo, poly(arylazo), stilbene, cyanostilbene, cinnamate or chalcone.

A photo-orientable substance may in particular be a monomer, a oligomer or a polymer. The photo-orientable moieties can, for example, be covalently bonded within the main chain or within a side chain of a polymer or oligomer or they may be part of a monomer or other compounds which are not polymerizable. A photo-orientable substance may further be a copolymer comprising different types of photo-orientable moieties or it may be a copolymer comprising side chains with and without photo-orientable moieties.

Polymers denotes for example to polyacrylate, polymethacrylate, polyimide, polyurethane, polyamic acids, polymaleinimide, poly-2-chloroacrylate, poly-2-phenylacrylate; unsubstituted or with $C_{1-6}$alkyl substituted poylacrylamide, polymethacyrlamide, poly-2-chloroacrylamide, poly-2-phenylacrylamide, polyether, polyvinylether, polyester, polyvinylester, polystyrene-derivatives, polysiloxane, straight-chain or branched alkyl esters of polyacrylic or polymethacrylic acids; polyphenoxyalkylacrylates, polyphenoxyalkylmethacrylates, polyphenylalkylmethacrylates with alkyl residues of 1-20 carbon atoms; polyacrylnitril, polymethacrylnitril, cycloolephinic polymers, polystyrene, poly-4-methylstyrene or mixtures thereof.

A photo-orientable substance may also comprise photosensitizers, for example, ketocoumarines and benzophenones.

Further, preferred photo-orientable monomers or oligomers or polymers are described in U.S. Pat. Nos. 5,539,074, 6,201,087, 6,107,427, 6,632,909 and 7,959,990.

Alignment of the LCP can be achieved by any other known means for aligning liquid crystals. For example, the support may have an aligning surface, which shall mean that the surface has the capability to align liquid crystals. The support may already provide the alignment without further treatment. For example, if a plastic substrate is used as a support, it may provide alignment on the surface due to the manufacturing method, for example extrusion or stretching of the substrate. It is also possible to brush the support or imprint a directional microstructure to generate alignment capability.

The steps of polymerizing the LCP compounds and exposure to aligning light may be in any sequence. Polymerization may be initiated before or after exposure to aligning light. Or polymerization and exposure may occur simultaneously.

A further embodiment of the present invention relates to a process for manufacturing an optical film comprising an anisotropic compound of formula (I), a LCP mixture or a LCP network according to the present invention, by exposure to aligning light, preferably by an energy of <200 mJ, more preferably of <150 mJ and more preferably <100 mJ.

The LCP mixture may be applied to the support by any suitable method like, extruding, casting, molding, 2D- or 3D-printing or coating. Suitable coating methods are, for example: spin-coating, blade coating, knife coating, kiss roll coating, die coating, dipping, brushing, casting with a bar, roller-coating, flow-coating, wire-coating, spray-coating, dip-coating, curtain-coating, air knife coating, reverse roll coating, gravure coating, metering rod (Meyer bar) coating, slot die (Extrusion) coating, roller coating, flexo coating. Suitable printing methods include: silk screen printing, relief printing such as flexographic printing, jet printing, intaglio printing such as direct gravure printing or offset gravure printing, lithographic printing such as offset printing, or stencil printing such as screen printing.

A further embodiment of the present invention is an optical film comprising an anisotropic compound of formula (I), or the LCP mixture, or LCP network according to the present invention. Preferably, the optical film comprises the aligned anisotropic compound of formula (I), or the LCP mixture, or LCP network. More preferred the alignment quality is uniform with no tilt domains.

Further preferred are optical films comprising LCPs according to the present invention which show reverse retardation pattern of polarized light over a wide wavelength band. The optical films according to the present invention have preferably birefringence with reverse wavelength dispersion: $Re_{450}/R_{550}$ is below 0.88, preferably $R_{450}/R_{550}$ is <0.85; whereas $Re_{650}/Re_{550}$ is above 1.01, preferably $Re_{650}/Re_{550}$ is >1.03. (The $Re_{450}$ represents the retardation of the film at a wavelength of 450 nm, $R_{550}$ the retardation of the film at a wavelength of 550 nm and $Re_{650}$ the retardation of the film at a wavelength of 650 nm).

The invention will now be described with reference to the following non-limiting examples. These examples are provided by way of illustration only. Variations on these examples falling within the scope of the invention will be apparent to a skilled person.

EXAMPLES

The following examples are provided to illustrate further and to facilitate understanding of the present invention and are not in any way intended to limit the invention.

Example 1

Synthesis of Compound 1

Synthesis of [3-formyl-4-[4-(6-prop-2-enoyloxy-hexoxy)benzoyl]oxy-phenyl] 4-(6-prop-2-enoyloxy-hexoxy)benzoate Oxalyl chloride (2.5 mL, 29 mmol) was added dropwise to a solution of 4-(6-acryloyloxy-hex-1-yloxy)benzoic acid (6.98 g, 24 mmol) in 48 mL of anhydrous toluene, 4 mg of 4-methoxyphenol and 1 mL of anhydrous DMF at 45° C. After 2 h, the reaction mixture was cooled down to 0° C. and added dropwise at 0-5° C. to a solution of 2,5-dihydroxy-benzaldehyde (1.5 g, 11 mmol) in 40 mL of anhydrous DMA and N,N-dimethylcyclohexylamine (7.8 g, 52 mmol). The reaction mixture was stirred at ambient temperature overnight. The orange solution was quenched by addition of 15 mL of water, extracted with dichloromethane and successively washed with water, brine, dried over sodium sulfate and concentrated under vacuum. The title compound was obtained as a white solid (4.19 g, 56%) after recrystallization from dichloromethane/methanol.

$^1$H NMR (400 MHz, DMSO-d6) δ 10.04 (s, 1H), 8.08 (m, 4H), 7.82 (d, 1H), 7.71 (dd, 1H), 7.54 (d, 1H), 7.10 (m, 4H), 6.26 (d, 1H), 6.15 (dd, 1H), 5.90 (d, 1H), 4.09 (m, 8H), 1.72 (m, 4H), 1.60 (m, 4H), 1.39 (m, 8H).

Synthesis of 2-hydrazinylquinoxaline

A microwave reaction vessel was charged with 2-chloro-quinoxaline (1.70 g, 15 mmol), hydrazine monohydrate (1.82 mL, 37.5 mmol) in dry ethanol (15 mL). The mixture was heated to 90° C. in a microwave reactor for 20 minutes. The reaction mixture was cooled down, and precipitates were filtered and washed with hexane to give the title compounds as an orange solid (2.07 g, 86%). $^1$H-NMR (400 MHz, DMSO-d6) δ 8.67 (s, 1H), 8.34 (s, 1H), 7.76 (d, J=8.2 Hz, 1H), 7.52-7.58 (m, 2H), 7.30-7.34 (m, 1H), 4.43 (s, 2H).

Synthesis of [4-[4-(6-prop-2-enoyloxyhexoxy)ben-zoyl]oxy-3-[(E)-(quinoxalin-2-ylhydrazono)methyl]phenyl] 4-(6-prop-2-enoyloxyhexoxy)benzoate compound 1

(±) 10-Camphorsulfonic acid (23.2 mg, 0.1 mmol) was added to a solution of [3-formyl-4-[4-(6-prop-2-enoyloxy-hexoxy)benzoyl]oxy-phenyl] 4-(6-prop-2-enoyloxyhexoxy)benzoate (0.69 g, 1.0 mmol) and 2-hydrazinylquinoxaline (0.19 g, 1.2 mmol) in 10 mL of dry tetrahydrofuran under an atmosphere of nitrogen. The resulting solution was stirred for 3 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a yellow solid (0.67 g, 81%) was obtained after recrystallization from dichloromethane/hexane.

$^1$H NMR (400 MHz, CDCl$_3$) δ 9.11 (s, 1H), 8.63 (s, 1H), 8.17-8.20 (m, 4H), 7.97 (d, J=8.2 Hz, 1H), 7.92-7.94 (m, 2H), 7.59-7.68 (m, 2H), 7.46-7.52 (m, 1H), 7.29 (s, 2H), 6.98-7.02 (m, 4H), 6.38-6.43 (m, 2H), 6.10-6.17 (m, 2H), 5.81-5.84 (m, 2H), 4.19 (t, J=6.6 Hz, 4H), 4.06-4.11 (m, 4H), 1.83-1.90 (m, 4H), 1.71-1.78 (m, 4H), 1.45-1.53 (m, 8H), MALDI-TOF (CHCA) 851.33 (M$^+$+Na).

Example 2

Synthesis of Compound 2

Synthesis of tert-butyl N-(quinoxalin-2-ylamino)carbamate

A solution of di-tert-butyl dicarbonate (3.9 g, 18 mmol) in dry THF (9 mL) was added to a solution of 2-hydrazinylqui-noxaline (2.4 g, 15 mmol) in dry THF (30 mL). The reaction mixture was stirred for 2 h at 50° C. The reaction mixture was cooled to room temperature and quenched with a saturated aqueous solution of sodium bicarbonate and extracted twice with 1:2 mixture of ethyl acetate and hexane. The organic layer was washed with brine, dried over anhydrous sodium sulfate and the solvent was removed under reduced pressure to give the title compound as a brown solid (4.11 g, quant.).

$^1$H NMR (400 MHz, DMSO-d6) δ 9.27 (s, 1H), 9.02 (s, 1H), 8.35 (s, 1H), 7.84 (d, J=8.2 Hz, 1H), 7.60-7.63 (m, 2H), 7.41-7.45 (m, 1H), 1.46 (s, 9H).

Synthesis of tert-butyl N-[methyl(quinoxalin-2-yl)amino]carbamate

Iodomethane (0.4 mL, 6.3 mmol) was added to a solution of [3-formyl-4-[4-(6-prop-2-enoyloxyhexoxy)benzoyl]oxy-phenyl] 4-(6-prop-2-enoyloxyhexoxy)benzoate (1.5 g, 5.8 mmol) in dry DMF (10 mL) at 0° C. Reaction mixture was stirred for 3 h at ambient temperature. The reaction mixture was quenched with water and extracted twice with 1:2 mixture of ethyl acetate and hexane. The organic layer was washed with water and brine, dried over anhydrous sodium sulfate and the solvent was removed under reduced pressure. The residue was purified by flash column chromatography over silica gel using a 1:2 mixture of ethyl acetate/hexane to give the title compound as a red oil (0.46 g, 21%). $^1$H NMR (400 MHz, DMSO-d6) δ 9.72 (s, 1H), 8.54 (s, 1H), 7.87 (d, J=7.8 Hz, 1H), 7.68-7.71 (m, 1H), 7.63-7.67 (m, 1H), 7.45-7.49 (m, 1H), 3.29 (s, 3H), 1.44 (s, 9H).

Synthesis of 1-methyl-1-quinoxalin-2-yl-hydrazine

Trifluoroacetic acid (TFA) (3 mL) was added to a solution of tert-butyl N-[methyl(quinoxalin-2-yl)amino]carbamate (0.43 g, 1.6 mmol) in dichoromethane (3 mL). Reaction mixture was stirred for 3 h at ambient temperature. Solvent was removed under reduced pressure and the residue was dissolved in dichloromethane and washed with a saturated aqueous solution of sodium bicarbonate and brine, dried over anhydrous sodium sulfate and the solvent was removed under reduced pressure to give the title compound as a yellow solid (0.25 g, 93%). $^1$H NMR (400 MHz, DMSO-d6) δ 9.02 (s, 1H), 7.90 (dd, J=8.2, 1.4 Hz, 1H), 7.69 (dd, J=8.2, 0.9 Hz, 1H), 7.55-7.59 (m, 1H), 7.37-7.42 (m, 1H), 4.14 (s, 2H), 3.47 (s, 3H).

Synthesis of [3-[(E)-[methyl(quinoxalin-2-yl)hydrazono]methyl]-4-[4-(6-prop-2-enoyloxyhexoxy)benzoyl]oxy-phenyl] 4-(6-prop-2-enoyloxyhexoxy)benzoate Compound 2

(±) 10-Camphorsulfonic acid (32 mg, 0.14 mmol) was added to a solution of 2-formyl-1,4-phenylene bis[4-(6-acryloyloxyhexyloxy)benzoate] (0.95 g, 1.4 mmol) and N-Methyl-N-(quinoxaline-2-yl)hydrazine (0.25 g, 1.5 mmol) in 14 mL of dry tetrahydrofuran under an atmosphere of nitrogen. The resulting solution was stirred for 3 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a yellow solid (0.92 g, 79%) was obtained after recrystallization from dichloromethane/hexane.

$^1$H NMR (400 MHz, DMSO-d6) δ 9.44 (s, 1H), 8.12-8.17 (m, 4H), 8.08 (d, J=2.7 Hz, 1H), 7.93 (s, 1H), 7.89 (d, J=8.2 Hz, 1H), 7.74-7.77 (m, 1H), 7.66-7.70 (m, 1H), 7.50-7.55 (m, 1H), 7.43 (d, J=8.7 Hz, 1H), 7.37 (dd, J=8.7, 2.7 Hz, 1H), 7.12-7.15 (m, 4H), 6.29-6.34 (m, 2H), 6.14-6.20 (m, 2H), 5.92-5.95 (m, 2H), 4.08-4.13 (m, 8H), 3.63 (s, 3H), 1.76 (s, 4H), 1.60-1.68 (m, 4H), 1.40-1.46 (m, 8H).

Example 2A

Synthesis of Compound 2A

Synthesis of tert-butyl N-[hexyl(quinoxalin-2-yl)amino]carbamate

A round-bottom flask was charged with tert-butyl N-(quinoxalin-2-ylamino) (1.36 g, 5 mmol), 1-iodohexane (0.88 mL, 6 mmol), potassium carbonate (1.04 g, 7.5 mmol), and dry DMF (10 mL). The mixture was stirred at 50° C. under an atmosphere of nitrogen for 18 h. The reaction mixture was cooled to ambient temperature, diluted with a mixture of ethyl acetate/hexane (1/2), washed with water three times and brine once. The organic layer was dried over anhydrous sodium sulfate and the solvent was removed under reduced pressure. The residue was purified by flash column chromatography on silica gel using ethyl acetate/hexane to give the title compound as brown oil (443 mg, 26%).

$^1$H-NMR (400 MHz, DMSO-d6) δ 9.72 (s, 1H), 8.46 (s, 1H), 7.85 (d, J=7.8 Hz, 1H), 7.61-7.67 (m, 2H), 7.43-7.47 (m, 1H), 1.57-1.64 (m, 2H), 1.45 (s, 9H), 1.24-1.33 (m, 8H), 0.83-0.87 (m, 3H)

Synthesis of 1-hexyl-1-quinoxalin-2-yl-hydrazine

Trifluoroacetic acid (TFA) (2.5 mL) was added to a solution of tert-butyl N-[hexyl(quinoxalin-2-yl)amino]carbamate (0.44 g, 1.3 mmol) in dichloromethane (2.5 mL). Reaction mixture was stirred for 19 h at ambient temperature. Solvent was removed under reduced pressure and the residue was dissolved in ethyl acetate and washed with a saturated aqueous solution of sodium bicarbonate and brine, dried over anhydrous sodium sulfate and the solvent was removed under reduced pressure to give the title compound as a beige oil (0.31 g, quant.).

$^1$H-NMR (400 MHz, DMSO-d6) δ 9.04 (s, 1H), 7.76 (d, J=7.8 Hz, 1H), 7.49-7.55 (m, 2H), 7.29-7.33 (m, 1H), 4.86 (s, 2H), 3.74-3.77 (m, 2H), 1.64-1.71 (m, 2H), 1.23-1.35 (m, 6H), 0.83-0.87 (m, 3H)

Synthesis of [3-[(E)-[hexyl(quinoxalin-2-yl)hydrazono]methyl]-4-[4-(6-prop-2-enoyloxyhexoxy)benzoyl]oxy-phenyl] 4-(6-prop-2-enoyloxyhexoxy)benzoate compound 2A (±) 10-Camphorsulfonic acid (26 mg, 0.11 mmol) was added to a solution of [3-[(E)-[methyl(quinoxalin-2-yl)hydrazono]methyl]-4-[6-prop-2-enoyloxyhexoxy)benzoyl]oxy-phenyl] 4-(6-prop-2-enoyloxyhexoxy)benzoate (0.74 g, 1.1 mmol) and 1-hexyl-1-quinoxalin-2-yl-hydrazine (0.31 g, 1.3 mmol) in dry tetrahydrofuran (10 mL) under an atmosphere of nitrogen. The resulting solution was stirred for 18 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a pale-yellow solid (0.70 g, 72%) was obtained after recrystallization from dichloromethane/hexane.

$^1$H-NMR (400 MHz, DMSO-d6) δ 9.47 (s, 1H), 8.18 (d, J=9.1 Hz, 2H), 8.13 (d, J=9.1 Hz, 2H), 8.10 (d, J=2.7 Hz, 1H), 7.88-7.91 (m, 2H), 7.73 (dd, J=8.5, 1.1 Hz, 1H), 7.65-7.69 (m, 1H), 7.50-7.54 (m, 1H), 7.44 (d, J=8.7 Hz, 1H), 7.38 (dd, J=8.7, 2.7 Hz, 1H), 7.15 (d, J=2.7 Hz, 2H), 7.12 (d, J=3.2 Hz, 2H), 6.32 (dd, J=17.4, 1.8 Hz, 2H), 6.17 (ddd, J=17.4, 10.3, 1.1 Hz, 2H), 5.93 (dd, J=10.5, 1.8 Hz, 2H), 4.24-4.28 (m, 2H), 4.07-4.13 (m, 8H), 1.72-1.80 (m, 4H), 1.59-1.68 (m, 4H), 1.36-1.50 (m, 10H), 0.95-1.11 (m, 6H), 0.72 (t, J=7.1 Hz, 3H).

Example 2B

Synthesis of Compound 2B

Synthesis of (3-formyl-4-hydroxy-phenyl) 4-propylcyclohexanecarboxylate

To a solution of 2,5-dihydroxybenzaldehyde (1.38 g, 10 mmol), trans-4-propylcyclohexane-carboxylic acid (1.79 g, 10.5 mmol) and 4-dimethylaminopyridine (DMAP) (122 mg, 1 mmol) in dry dichloromethane (20 mL), 1-(3-dimethylaminopropyl)-3-ethylcarbodiimide (EDC) (1.94 mL, 11 mmol) was added slowly. The reaction mixture was stirred for 22 h at ambient temperature. The reaction mixture was quenched with a saturated aqueous solution of sodium bicarbonate and extracted with dichloromethane. The organic phase was washed with brine, dried over anhydrous sodium sulfate and the solvent was removed under reduced pressure. The residue was purified by flash column chromatography on silica gel using ethyl acetate/hexane to give the title compound as a yellow solid (1.31 g, 45%).

$^1$H-NMR (400 MHz, CDCl$_3$) δ 10.90 (s, 1H), 9.85 (s, 1H), 7.31 (d, J=2.7 Hz, 1H), 7.23 (dd, J=9.1, 2.7 Hz, 1H), 6.99 (d, J=9.1 Hz, 1H), 2.44-2.52 (m, 1H), 2.11-2.15 (m, 2H), 1.86-1.90 (m, 2H), 1.50-1.57 (m, 2H), 1.29-1.39 (m, 3H), 1.17-1.23 (m, 2H), 0.97-1.04 (m, 3H), 0.87-0.92 (m, 3H)

Synthesis of [2-formyl-4-(4-propylcyclohexanecarbonyl)oxy-phenyl] 4-(6-prop-2-enoyloxyhexoxy) benzoate To a solution of (3-formyl-4-hydroxy-phenyl) 4-propylcyclohexanecarboxylate (1.3 g, 4.5 mmol), 4-(6-acryloyloxy-hex-1-yloxy)benzoic acid (1.38 g, 4.70 mmol) and 4-dimethylaminopyridine (DMAP) (55 mg, 0.45 mmol) in dry dichloromethane (9 mL), 1-(3-dimethylaminopropyl)-3-ethylcarbodiimide (EDC) (0.87 mL, 4.93 mmol) was added. The reaction mixture was stirred for 5 h at ambient temperature. The reaction mixture was quenched with a saturated aqueous solution of sodium bicarbonate and extracted with ethyl acetate. The organic phase was washed with brine, dried over anhydrous sodium sulfate and the solvent was removed under reduced pressure. The residue was purified by flash column chromatography on silica gel using ethyl acetate/hexane to give the title compound as a beige oil (2.73 g) containing some impurities, which was used for the next reaction without further purification.

Synthesis of [2-[(E)-[methyl(quinoxalin-2-yl)hydrazono]methyl]-4-(4-propylcyclohexanecarbonyl)oxy-phenyl] 4-(6-prop-2-enoyloxyhexoxy)benzoate Compound 2B (±) 10-Camphorsulfonic acid (105 mg, 0.45 mmol) was added to a solution of [3-formyl-4-(4-propylcyclohexanecarbonyl)oxy-phenyl] 4-(6-prop-2-enoyloxyhexoxy)benzoate (2.73 g, 4.5 mmol), 1-methyl-1-quinoxalin-2-yl-hydrazine (0.82 g, 4.7 mmol), and 4-hydroxy-2,2,6,6-tetramethylpiperidine 1-oxyl free radical (TEMPO-OH) (9 mg, 0.05 mmol) in dry tetrahydrofuran (45 mL) under an atmosphere of nitrogen. The resulting solution was stirred for 24 h at ambient temperature. The reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a gray solid (1.61 g, 50%) was obtained after recrystallization from dichloromethane/hexane.

$^1$H-NMR (400 MHz, DMSO-d6) δ 9.39 (s, 1H), 8.14 (d, J=9.1 Hz, 2H), 7.90-7.92 (m, 2H), 7.85-7.86 (m, 1H), 7.75-7.77 (m, 1H), 7.67-7.71 (m, 1H), 7.52-7.56 (m, 1H), 7.39 (d, J=8.7 Hz, 1H), 7.20 (dd, J=8.7, 2.7 Hz, 1H), 7.12 (d, J=8.7 Hz, 2H), 6.32 (dd, J=17.2, 1.6 Hz, 1H), 6.17 (dd, J=17.4, 10.5 Hz, 1H), 5.93 (dd, J=10.3, 1.6 Hz, 1H), 4.07-4.13 (m, 4H), 3.62 (s, 3H), 2.11-2.15 (m, 2H), 1.72-1.84 (m, 4H), 1.61-1.68 (m, 2H), 1.37-1.54 (m, 7H), 1.27-1.35 (m, 3H), 1.16-1.21 (m, 2H), 0.95-1.04 (m, 2H), 0.87 (t, J=7.1 Hz, 3H)

Example 2C

Synthesis of Compound 2C

Synthesis of 2-[amino(quinoxalin-2-yl)amino]ethanol

A microwave reaction vessel was charged with 2-chloroquinoxaline (0.82 g, 5 mmol) and 2-hydrazinoethanol (0.85 mL, 12.5 mmol) in dry EtOH (2.5 mL). The mixture was heated to 90° C. in a microwave reactor for 10 min. The reaction mixture was quenched with a saturated aqueous solution of sodium bicarbonate and extracted with dichloromethane. The organic phase was washed with brine, dried over anhydrous sodium sulfate and the solvent was removed under reduced pressure. The residue was washed with hexane to give the title compound as a yellow solid (0.59 g, 58%).

$^1$H-NMR (400 MHz, DMSO-d6) δ 9.05 (s, 1H), 7.77 (d, J=8.2 Hz, 1H), 7.51-7.54 (m, 2H), 7.30-7.34 (m, 1H), 4.91 (s, 2H), 4.79 (t, J=5.3 Hz, 1H), 3.86 (t, J=5.9 Hz, 2H), 3.73 (q, J=5.6 Hz, 2H)

Synthesis of [3-[(E)-[2-hydroxyethyl(quinoxalin-2-yl)hydrazono]methyl]-4-[4-(6-prop-2-enoyloxyhexoxy)benzoyl]oxy-phenyl] 4-(6-prop-2-enoyloxyhexoxy)benzoate Compound 2C (±) 10-Camphorsulfonic acid (46 mg, 0.2 mmol) was added to a solution of [3-formyl-4-[4-(6-prop-2-enoyloxyhexoxy)benzoyl]oxy-phenyl] 4-(6-prop-2-enoyloxyhexoxy)benzoate (1.37 g, 2 mmol), 2-[amino(quinoxalin-2-yl)amino]ethanol (0.43 g, 2.1 mmol), and 4-hydroxy-2,2,6,6-tetramethylpiperidine 1-oxyl free radical (TEMPO-OH) (3 mg, 0.02 mmol) in dry tetrahydrofuran (20 mL) under an atmosphere of nitrogen. The resulting solution was stirred for 23 h at ambient temperature. The reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a yellow solid (1.46 g, 83%) was obtained after recrystallization from dichloromethane/methanol.

$^1$H-NMR (400 MHz, DMSO-d6) δ 9.42 (s, 1H), 8.26 (s, 1H), 8.12-8.16 (m, 4H), 8.05 (d, J=2.7 Hz, 1H), 7.89 (d, J=8.2 Hz, 1H), 7.74 (dd, J=8.2, 0.9 Hz, 1H), 7.65-7.69 (m, 1H), 7.50-7.54 (m, 1H), 7.44 (d, J=8.7 Hz, 1H), 7.37 (dd, J=8.7, 2.7 Hz, 1H), 7.10-7.15 (m, 4H), 6.32 (dd, J=17.2, 1.6 Hz, 2H), 6.17 (dd, J=17.4, 10.1 Hz, 2H), 5.93 (dd, J=10.1, 1.8 Hz, 2H), 4.86 (t, J=5.3 Hz, 1H), 4.41 (t, J=5.9 Hz, 2H), 4.07-4.14 (m, 8H), 3.63 (q, J=5.6 Hz, 2H), 1.72-1.80 (m, 4H), 1.59-1.68 (m, 4H), 1.37-1.49 (m, 8H).

Example 2D

Synthesis of Compound 2D

Synthesis of 1-cyclohexyl-1-quinoxalin-2-yl-hydrazine

A microwave reaction vessel was charged with 2-chloroquinoxaline (1.65 g, 10 mmol) and cyclohexylhydrazine hydrochloride (1.81 g, 12 mmol) in triethylamine (10 mL). The mixture was heated to 90° C. in a microwave reactor for 20 min. The reaction mixture was quenched with a saturated aqueous solution of sodium bicarbonate and extracted with ethyl acetate. The organic phase was washed with water and brine, dried over anhydrous sodium sulfate and the solvent was removed under reduced pressure. The residue was washed with hexane to give the title compound as a yellow solid (0.70 g, 29%).

$^1$H-NMR (400 MHz, CDCl$_3$) δ 8.98 (s, 1H), 7.86-7.89 (m, 1H), 7.65-7.68 (m, 1H), 7.53-7.57 (m, 1H), 7.35-7.39 (m, 1H), 4.46-4.53 (m, 1H), 3.85 (s, 2H), 1.88-1.92 (m, 2H), 1.64-1.81 (m, 5H), 1.45-1.56 (m, 2H), 1.14-1.26 (m, 1H)

Synthesis of [3-[(E)-[cyclohexyl(quinoxalin-2-yl) hydrazono]methyl]-4-[4-(6-prop-2-enoyloxyhexoxy) benzoyl]oxy-phenyl] 4-(6-prop-2-enoyloxyhexoxy) benzoate Compound 2D (±) 10-Camphorsulfonic acid (33 mg, 0.14 mmol) was added to a solution of [3-formyl-4-[4-(6-prop-2-enoyloxy-hexoxy)benzoyl]oxy-phenyl] 4-(6-prop-2-enoyloxyhexoxy) benzoate (0.97 g, 1.42 mmol), 1-cyclohexyl-1-quinoxalin-2-yl-hydrazine (0.36 g, 1.5 mmol), and 4-hydroxy-2,2,6,6-tetramethylpiperidine 1-oxyl free radical (TEMPO-OH) (2 mg, 0.01 mmol) in dry tetrahydrofuran (14 mL) under an atmosphere of nitrogen. The resulting solution was stirred for 23 h at ambient temperature. The reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a yellow solid (1.18 g, 91%) was obtained after recrystallization from dichloromethane/methanol.

$^1$H-NMR (400 MHz, DMSO-d6) δ 9.34 (s, 1H), 8.26 (s, 1H), 8.17 (d, J=6.9 Hz, 2H), 8.13 (d, J=9.1 Hz, 2H), 8.01 (d, J=2.7 Hz, 1H), 7.87 (d, J=9.1 Hz, 1H), 7.69 (dd, J=8.2, 1.4 Hz, 1H), 7.65 (td, J=7.5, 1.4 Hz, 1H), 7.51-7.55 (m, 1H), 7.45 (d, J=8.7 Hz, 1H), 7.38 (dd, J=8.9, 3.0 Hz, 1H), 7.13-7.15 (m, 2H), 7.11-7.12 (m, 2H), 6.32 (dd, J=17.4, 1.8 Hz, 2H), 6.13-6.20 (m, 2H), 5.93 (dd, J=10.3, 1.6 Hz, 2H), 4.86-4.94 (m, 1H), 4.07-4.13 (m, 8H), 2.15-2.25 (m, 2H), 1.72-1.79 (m, 4H), 1.61-1.68 (m, 8H), 1.37-1.50 (m, 9H), 1.21 (q, J=13.0 Hz, 2H), 0.68-0.77 (m, 1H).

Example 2E

Synthesis of Compound 2E

Synthesis of 2,5-dihydroxy-4-methyl-benzaldehyde

To a suspension of paraformaldehyde (2.1 g, 70 mmol), magnesium chloride (1.43 g, 15 mmol), triethylamine (5.6 mL, 40 mmol) in dry acetonitrile (15 mL), methylhydroquinone (1.24 g, 10 mmol) was added. The mixture was refluxed with stirring under an atmosphere of nitrogen for 17 h. The reaction mixture was cooled to ambient temperature, quenched with 1 N HCl aq, extracted with ethyl acetate, washed with brine. The organic layer was dried over anhydrous sodium sulfate and the solvent was removed under reduced pressure. The residue was purified by flash column chromatography on silica gel using ethyl acetate/hexane to give the title compound as a yellow solid (0.31 g, 20%).

$^1$H-NMR (400 MHz, MeOD) δ 9.85 (s, 1H), 6.95 (s, 1H), 6.70 (s, 1H), 2.21 (s, 3H).

Synthesis of [2-formyl-5-methyl-4-[4-(6-prop-2-enoyloxyhexoxy)benzoyl]oxy-phenyl] 4-(6-prop-2-enoyloxyhexoxy)benzoate To a solution of 4-(6-acryloyloxy-hex-1-yloxy)benzoic acid (2.19 g, 7.5 mmol) and 4-methoxyphenol (47 mg, 0.4 mmol) in anhydrous toluene (15 mL) and anhydrous dimethylformamide (DMF) (0.3 mL), oxalyl chloride (0.77 mL, 9 mmol) was added dropwise for 15 min at 45° C. After stirring for 19 h, the reaction mixture was cooled down to ambient temperature and added dropwise for 20 min at 0-5° C. to a solution of Building block K (0.51 g, 3.4 mmol) and N,N-dimethylcyclohexylamine (2.5 mL, 17 mmol) in anhydrous dimethylacetamide (11 mL). The reaction mixture was stirred at ambient temperature for 3 h. The reaction mixture was quenched by addition of 1 M HCl aq. and water on ice bath, extracted with dichloromethane and successively washed with water, brine, dried over sodium sulfate and concentrated under vacuum. The title compound was obtained as a pink solid (1.38 g, 59%) after recrystallization from dichloromethane/methanol.

$^1$H-NMR (400 MHz, CDCl$_3$) δ 10.15 (s, 1H), 8.15-8.18 (m, 4H), 7.71 (s, 1H), 6.98-7.01 (m, 5H), 6.41 (dd, J=17.4, 1.4 Hz, 2H), 6.13 (dd, J=17.4, 10.5 Hz, 2H), 5.83 (dd, J=10.3, 1.6 Hz, 2H), 4.15-4.21 (m, 8H), 4.07 (t, J=5.9 Hz, 8H), 2.32 (s, 3H), 1.81-1.89 (m, 4H), 1.69-1.77 (m, 4H), 1.48-1.54 (m, 8H).

Synthesis of [5-methyl-2-[(E)-[methyl(quinoxalin-2-yl)hydrazono]methyl]-4-[4-(6-prop-2-enoyloxy-hexoxy)benzoyl]oxy-phenyl] 4-(6-prop-2-enoyloxy-hexoxy)benzoate Compound 2E (±) 10-Camphorsulfonic acid (44 mg, 0.19 mmol) was added to a solution of [2-formyl-5-methyl-4-[4-(6-prop-2-enoyloxyhexoxy)benzoyl]oxy-phenyl]4-(6-prop-2-enoyloxyhexoxy)benzoate (1.3 g, 1.9 mmol), 1-methyl-1-quinoxalin-2-yl-hydrazine (0.34 g, 2.0 mmol), and 4-hydroxy-2,2,6,6-tetramethylpiperidine 1-oxyl free radical (TEMPO-OH) (4 mg, 0.02 mmol) in dry tetrahydrofuran (20 mL) under an atmosphere of nitrogen. The resulting solution was stirred for 22 h at ambient temperature. The reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a yellow solid (1.20 g, 75%) was obtained after recrystallization from dichloromethane/hexane.

$^1$H-NMR (400 MHz, DMSO-d6) δ 9.41 (s, 1H), 8.14-8.16 (m, 4H), 8.01 (s, 1H), 7.87-7.89 (m, 2H), 7.73-7.75 (m, 1H), 7.65-7.69 (m, 1H), 7.49-7.53 (m, 1H), 7.34 (s, 1H), 7.11-7.15 (m, 4H), 6.32 (dd, J=17.2, 1.6 Hz, 2H), 6.17 (dd, J=17.4, 10.5 Hz, 2H), 5.93 (dd, J=10.3, 1.6 Hz, 2H), 4.07-4.14 (m, 8H), 3.61 (s, 3H), 2.20 (s, 3H), 1.72-1.80 (m, 4H), 1.59-1.68 (m, 4H), 1.36-1.51 (m, 8H).

Example 3

The phase transition temperatures and mesophase textures were determined by differential scanning calorimetry and polarized optical microscopy as described below using compounds of examples 1 to 2E and compared to compound R1 described in patent publication WO2012/141245.

Polarized Optical Microscopy Measurements:

3 mg of each compound was placed between two glass slides in a hot stage oven and heated from 25° C. to 200° C.

then cooled down again to 25° C. Characteristic birefringent textures were analyzed using a polarized optical microscope. Glass coated substrate with a rubbed polyimide layer were also used to confirm the mesophase behavior of the compounds.

Differential Scanning Calorimetry Measurements:

Approximately 5 mg of each compound placed in a sealed aluminum pan was subjected to two successive heating-cooling circles at a scanning rate of 10° C./min. The transition temperatures were determined from the resulting endo/exothermic peaks of the DSC thermograms.

All phase transition results are summarized in Table 1. Compound states are indicated as "Cr" for solid crystal phase, "N" for nematic and "Iso" for the isotropic liquid state.

TABLE 1

| Compound | Heating stage (° C.) | | Cooling Stage (°) | |
| --- | --- | --- | --- | --- |
| | Tcr-N | TN-iso | TN-iso | Tcr-N |
| R1 | 102 | 165 | 50 | 140 |
| 1 | 128 | 140 | 137 | <30 |
| 2 | 109 | 115 | 99 | <30 |
| 2A | 95 | 97 | 84 | 56 |
| 2B | 107 | 120 | 104 | 80 |
| 2C | 113 | 114 | 109 | 100 |
| 2D | 83 | 86 | 84 | <30 |
| 2E | 88 | 93 | 82 | 60 |

Example 4

Preparation of the Optical Film

General procedure for LCP-coated film preparation on rubbed substrate and evaluation 0.26 g of liquid crystal compound was dissolved in 830 μL of cyclopentanone. 13 μL of a 1 wt. % of cyclopentanone solution of BYK361 was added and the resulting solution was filtered through a 0.45 μm PTFE filter. 13 mg of Irgacure 907 was added to yield a polymerizable composition (1-2).

Each polymerizable composition was applied to a glass substrate coated a rubbed polyimide layer (manufactured by EHC). After drying/annealing the film for 4 minutes at the temperature shown in Table 2. The film was photocured using a UV spot cure (SP-7 manufactured by Ushio) at a dose of 1000 mJ/cm². UV exposure was performed at temperatures described in Table 2.

TABLE 2

| Compounds | Alignment temperature (° C.) | Curing Temperature (° C.) |
| --- | --- | --- |
| 1 | 100 | 25 |
| 2 | 120 | 80 |
| 2B | 120 | 90 |
| 2D | 90 | 25 |

Example 5

Retardation in the visible region (400-700 nm) was measured by polarization rotation method using a polarized optical microscope, Senarmont compensator and optical filters. In plane retardation $R_0$ is determined using the following equation from the extinction position $\theta$ at a certain wavelength $\lambda$.

$$R_0 = \frac{\theta}{180}\lambda$$

Film thickness d is measured using a Dektak® stylus profilers from Bruker. Film birefringence Δn is derived from the equation: $R_0 = \Delta n \cdot d$ The results show that the liquid crystal film was produced with a retardation that increases in association with an increase of the wavelength in the visible light region. The results are shown in FIG. 1 where the wavelength dispersion of the birefringence for examples 1, 2, 2B and 2D is plotted.

Example 6

General procedure for LCP-coated film preparation on photoalignment layer for the compounds R1, 1, 2, 2A, 2B, 2D and 2E:

Preparation of an Orientation Layer Using Photoalignment Materials:

A glass substrate was spin-coated with a photoalignment composition (2% solid content of photoaligning polymer in cyclopentanone as described in the application example on page 40 of patent publication WO2012/085048). The film was dried at 80° C. for 30 s and the resulting film thickness was about 100 nm. Then the film was exposed to aligning light, which was collimated and linearly polarized UV (LPUV) light (280-320 nm) with 500 mJ/cm². The plane of polarization was 0° with regard to a reference edge on the substrate.

Preparation of LCP Formulation:

A 15.0 w % solution of LCP is prepared by mixing 14.325 w % of LCP, 0.075 w % of inhibitor 2,6-di-tert-butyl-4-methylphenol (to prevent premature polymerisation), 0.45 w % of photoinitiator Irgacure 369, 0.15 w % of Tinuvin 123 in cyclohexanone and stirred thoroughly till the solid is completely dissolved at room temperature. The coating liquid was applied onto a glass plate with the above orientation layer to form a liquid crystal film by spin coating. After drying the film for a period and a temperature shown in Table 3, the sample is cooled down to room temperature. It was then photo-polymerised by irradiation with UV light (with Mercury lamp) for approximately a time and at a temperature indicated in the table 3.

TABLE 3

| Compounds | Time (mn) | Alignment temperature (° C.) | Curing Temperature (° C.) |
| --- | --- | --- | --- |
| 1 | 2 | 128 | 25 |
| 2 | 5 | 125 | 25 |
| 2A | 5 | 100 | 76 |
| 2B | 5 | 99 | 25 |
| 2D | 2 | 66 | 25 |
| 2E | 5 | 70 | 25 |

Example 7

Figure 2:
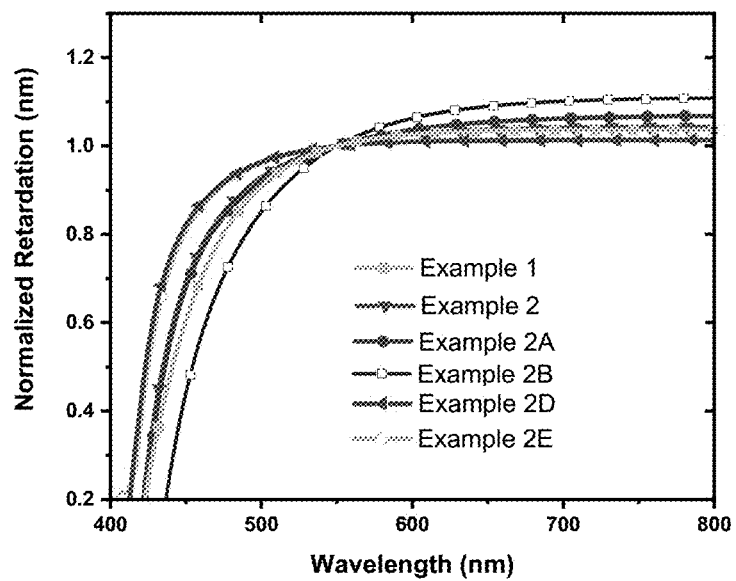
FIG. 2 shows the retardation dispersion of the films of example 6.

The retardation of the films made in example 6 was measured by Ellipsometry. The FIG. 2 indicates the retardation dispersion of the films made in example 6.

The results described above showed that liquid crystal film produced with the exemplified compounds showed a retardation that increases in association with an increase of the wavelength in the visible light region.

Table 4 shows the values of $Re_{450}/R_{550}$ and $Re_{650}/Re_{550}$ for each sample. The $Re_{450}$ represents the retardation of the film at a wavelength of 450 nm, $Re_{550}$ the retardation of the film at a wavelength of 550 nm and $Re_{650}$ the retardation of the film at a wavelength of 650 nm.

TABLE 4

| Liquid crystal example | $Re_{450}/Re_{550}$ | $Re_{650}/Re_{550}$ |
| --- | --- | --- |
| Comparative example R1 | 0.90 | 1.00 |
| Example 1 | 0.62 | 1.03 |
| Example 2 | 0.69 | 1.04 |
| Example 2A | 0.69 | 1.05 |
| Example 2B | 0.46 | 1.09 |
| Example 2D | 0.82 | 1.01 |
| Example 2E | 0.82 | 1.01 |

Table 4 shows results of retardation characteristics of the liquid crystal composition film. For improving color a value of $Re_{650}/Re_{550}$ higher than 1.00 and below 1.2 is preferred. The $Re_{650}/Re_{550}$ of the liquid crystal polymerisation films made with compounds from example 1, example 2, example 2A, example 2B, example 2D, example 2E was found to be significantly higher than the $Re_{650}/Re_{550}$ of liquid crystal composition of the comparative example R1 with all $Re_{650}/Re_{550}$ values above 1.01 and up to 1.09. In addition, a $Re_{450}/Re_{550}$ value below 0.90 is preferred.

Example 8

A 30.0 wt % solution of compound 2B was prepared by mixing 22.635 wt % compound 2B, 0.015 wt % of inhibitor 2,6-di-tert-butyl-4-methylphenol, 0.9 wt % of photoinitiator Irgacure® Oxe 03 (manufactured by BASF Corporation), 0.45 wt % of Tego® flow 425, 6 wt % of 05-[4-[3-methyl-4-[4-[5-oxo-5-(2-prop-2-enoyloxyethoxy)pentanoyl] oxy-benzoyl]oxy-phenoxy]carbonylphenyl] 01-(2-prop-2-enoyloxyethyl) pentanedioate LCP1, described in the patent US2012114907, in cyclohexanone and stirred thoroughly till the solid was completely dissolved at room temperature. The film was prepared as described in example 20 and was dried at 97° C. for 2 min onto a temperature controlled hot plate. The resulting film exhibited a good alignment quality.

Example 9

A 30.0 wt % solution of compound 2B was prepared by mixing 25.635 wt % compound 2B, 0.015 wt % of inhibitor 2,6-di-tert-butyl-4-methylphenol, 0.90 wt % of Irgacure® Oxe03, 0.45 wt % of Tego® flow 425, 3 wt % of [4-[6-(4-prop-2-enoyloxybutoxycarbonyloxy)naphthalene-2-carbonyl]oxyphenyl] 6-(4-prop-2-enoyloxybutoxycarbonyloxy) naphthalene-2-carboxylate LCP2 (described in U.S. Pat. No. 7,670,505 B2) in cyclohexanone and stirred thoroughly till the solid was completely dissolved at room temperature. The film was prepared as described in example 20 and was dried at 105° C. for 2 min onto a temperature controlled hot plate. The resulting film exhibited a good alignment quality.

Example 10

The retardation of the samples described in example 8 and 9 was measured with an Ellipsometer. Table 5 shows the results of the retardation characteristics for the different films depending on the liquid crystal composition.

TABLE 5

| Example | Compound | LCP | $Re_{450}/Re_{550}$ | $Re_{650}/Re_{550}$ |
| --- | --- | --- | --- | --- |
| 8 | 2B | 1 | 0.88 | 1.00 |
| 9 | 2B | 2 | 0.86 | 1.01 |

When using the liquid crystal composition film described in example 8 and 9 is found to be possible to fine-tune the retardation and to obtain $Re_{450}/R_{550}$ and $Re_{650}/Re_{550}$ values on request by modifying the proportion of the different components of the liquid crystal composition.

The invention claimed is:
1. An anisotropic compound of formula (I)

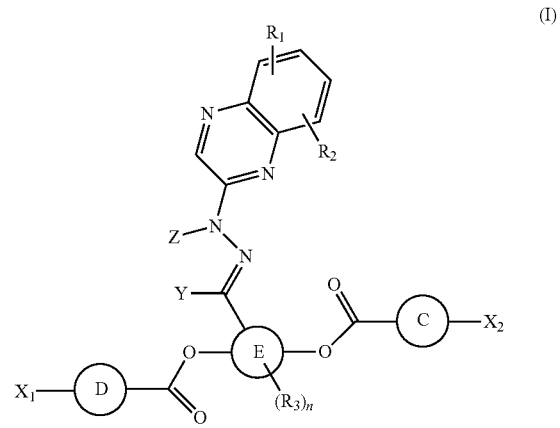

(I)

wherein
$R_1$, $R_2$ and $R_3$ are independently from each other selected from the group consisting of hydrogen, $C_1$-$C_{12}$ straight alkyl chain, $C_3$-$C_{12}$ branched alkyl chain, $C_3$-$C_{12}$ alkenyl, $C_1$-$C_{12}$ alkoxy, $C_3$-$C_{12}$ alkenyloxy, —$(CH_2)_m$—$C(CH_3)_3$, $NO_2$, CN, COR, —COOR, —OCOR, —CONR'R, —NR'COR, OCOOR, —OCONR'R, —NR'COOR, —F, —Cl, —$CF_3$ and —$OCF_3$;
in which
m is an integer between 0 and 12;
R is selected from the group consisting of hydrogen, an $C_{1-8}$ alkyl group, an $C_{3-18}$ alkenyl group, —$(CH_2)_p$—C—$(CF_3)_3$, CN and unsubstituted or substituted phenyl ring, wherein the substituent of the phenyl ring is selected from the group consisting of $C_1$-$C_6$ straight alkyl chain, or $C_3$-$C_6$ branched alkyl chain, $C_1$-$C_6$ alkoxy, — C—$(CH_3)_3$, halogen, —$CF_3$, $NO_2$, CN, COR''', —COOR''', —COOR''', —CONR''R''', —NR''COR''', OCOOR''', —COONR''R''', —NR''COOR''', —F, —Cl, —$CF_3$ and —$OCF_3$;
in which
R'' is selected from the group consisting of hydrogen, a lower alkyl group and a lower alkenyl group;
R''' is selected from the group consisting of hydrogen, an $C_{1-18}$ alkyl group and an $C_{3-18}$ alkenyl group;
p is an integer between 0 and 12;
R' is selected from the group consisting of hydrogen, lower alkyl, lower alkenyl and lower alkoxy;
n is 0, 1, 2 or 3;
Y is selected from the group consisting of H, or substituted or unsubstituted alkyl group having 1 to 12 carbon atoms;
Z is selected from the group consisting of hydrogen, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, wherein one or more carbon atoms may be replaced by —O—, —COO—, —OCO—, —OOC—, —O(CO)O—, —N—, —NR$^a$—, —CON—, —CO—R$^b$, —NH—R$^c$, wherein R$_a$ is a C$_1$-C$_{12}$ alkyl group, R$^b$ and R$^c$ are independently from each other a substituted or unsubstituted alkyl group having 1 to 20 carbon atoms, or an organic group having 6 to 30 carbon atoms that includes at least one aromatic ring, or a substituted or unsubstituted alkenyl group having 2 to 20 carbon atoms, or a substituted or unsubstituted cycloalkyl group having 3 to 12 carbon atoms;

rings C and D are independently from each other selected from the group consisting of phenyl, biphenyl, naphthyl, cycloalkyl, bicycloalkyl,

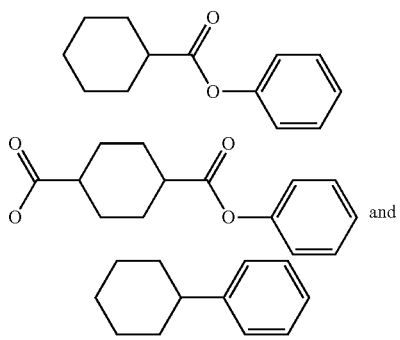

and with the proviso that at least one of rings C or D contains an aromatic ring;

ring E is selected from the group consisting of phenyl, biphenyl and naphthyl;

substituents X$_1$ and X$_2$ are independently from each other selected from the group consisting of hydrogen, C$_1$-C$_{12}$ substituted or unsubstituted straight alkyl chain, C$_3$-C$_{12}$ substituted or unsubstituted branched alkyl chain, C$_3$-C$_{12}$ substituted or unsubstituted straight chain or branched alkenyl chain and C$_1$-C$_{12}$ alkoxy, wherein one or more carbon atoms may be replaced by —O—, —COO—, —OCO—, —OOC—, —O(CO)O—, —N—, —NR—, —CON—, wherein R is a C$_1$-C$_{12}$ alkyl group;

or substituents X$_1$ and X$_2$ independently from each other are represented by the group of formula (II)

 (formula II)

wherein in the group of formula (II), n is an integer between 0 and 24, and one or more carbon atoms may be replaced by —O—, —COO—, —OCO—, —OOC—, —O(CO)O—, —N—, —NR—, —CON—, wherein R is a C$_1$-C$_{12}$ alkyl group;

PG in the group of formula (II) represents a polymerisable group selected from the group consisting of CH$_2$=C(Ph)-, CH$_2$=CW—COO—, CH$_2$=CH—COO-Ph-, CH$_2$=CW—CO—NH—, CH$_2$=CH—O—, CH$_2$=CH—OOC—, Ph-CH=CH—, CH$_2$=CH-Ph-, CH$_2$=CH-Ph-O—, R$^3$-Ph-CH=CH—COO—, R$_3$—OOC—CH=CH-Ph-O— and 2-W-epoxyethyl; in which W represents H, Cl, Ph or a lower alkyl and R$^3$ represents a lower alkyl with the proviso that when R$^3$ is attached to a phenylene group (-Ph-) it may also represent hydrogen or a lower alkoxy.

2. The anisotropic compound according to claim 1, wherein R$_1$, R$_2$ and R$_3$ are independently from each other selected from the group consisting of hydrogen, lower alkyl, lower alkenyl, lower alkoxy, lower alkenyloxy, —F, and —CF$_3$.

3. The anisotropic compound according to claim 2, wherein R$_1$, R$_2$ and R$_3$ are independently from each other selected from the group consisting of methyl, methoxy, —F, —C—(CH$_3$)$_3$ and —CF$_3$.

4. The anisotropic compound according to claim 1, wherein rings C and D are independently from each other phenyl or cyclohexyl, with the proviso that at least one is phenyl.

5. The anisotropic compound according to claim 4, wherein both rings C and D are phenyl rings.

6. The anisotropic compound according to claim 1, wherein ring E is a phenyl ring.

7. The compound according to claim 1, wherein the group of formula (II) representing X$_1$ and X$_2$ is independently from each other selected from the group consisting of

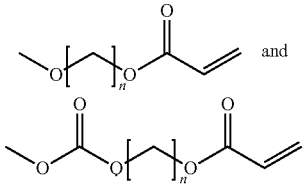

wherein n is an integer between 0 and 2, if rings C or D are aromatic rings or contain an aromatic ring; or the group of formula (II) representing X$_1$ and X$_2$ is independently from each other selected from the group consisting of, a hydrogen, C$_1$-C$_{12}$ substituted or unsubstituted straight alkyl chain, C$_3$-C$_{12}$ substituted or unsubstituted branched alkyl chain, C$_3$-C$_{12}$ substituted or unsubstituted straight chain or branched alkenyl chain and C$_1$-C$_{12}$ alkoxy, if rings C or D independently from each other are a cyclohexyl or contain a cyclohexyl, with the proviso that at least one ring C or D is an aromatic ring or a phenyl ring or contains an aromatic ring or a phenyl ring.

8. The anisotropic compound according to claim 1, wherein Z is selected from the group consisting of hydrogen and substituted or unsubstituted alkyl group having 1 to 12 carbon atoms.

9. The anisotropic compound according to claim 1, wherein PG is selected from acrylate or methacrylate.

10. An LCP mixture comprising the anisotropic compound of formula (I) according to claim 1.

11. The LCP mixture according to claim 10 which is in cross-linked or polymerised form.

12. An LCP network comprising the compound according to claim 1.

13. A process for manufacturing an optical film comprising an anisotropic compound according to claim 1, by exposing the anisotropic compound to aligning light.

14. An optical film comprising the anisotropic compound of formula (I) of claim 1.

15. A method of using the compound according to claim 1, comprising manufacturing an optical or an electro-optical device with the compound.

16. An optical or electro-optical device including the compound according to claim 1.

* * * * *